United States Patent
de la Mettrie et al.

(10) Patent No.: US 6,527,814 B1
(45) Date of Patent: *Mar. 4, 2003

(54) OXIDATION DYE COMPOSITION FOR KERATIN FIBERS, COMPRISING AN ANIONIC AMPHIPHILIC POLYMER

(75) Inventors: Roland de la Mettrie, Le Vesinet; Françoise Boudy, Paris, both of (FR)

(73) Assignee: L'Oreal S.A., Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/574,226

(22) Filed: May 19, 2000

Related U.S. Application Data

(63) Continuation of application No. 09/436,985, filed on Nov. 9, 1999, now abandoned, which is a continuation of application No. 09/362,092, filed on Jul. 28, 1999, now abandoned, which is a continuation of application No. 09/292,965, filed on Apr. 16, 1999, now Pat. No. 6,074,439, which is a continuation of application No. 08/859,257, filed on May 20, 1997, now Pat. No. 5,976,195.

(30) Foreign Application Priority Data

Sep. 6, 1996 (FR) ............................................. 96 10920

(51) Int. Cl.⁷ ................................................ A61K 7/13
(52) U.S. Cl. ...................... 8/405; 8/409; 8/410; 8/411; 8/412; 8/557; 8/558
(58) Field of Search ............................ 8/411, 405, 409, 8/410, 412, 557, 558

(56) References Cited

U.S. PATENT DOCUMENTS

| | | | |
|---|---|---|---|
| 3,200,040 A | 8/1965 | Lange | 167/86 |
| 3,530,215 A | 9/1970 | Grief et al. | 424/70 |
| 3,971,391 A | 7/1976 | Bore et al. | 132/7 |
| 3,973,901 A | 8/1976 | Micchelli et al. | 8/10 |
| 3,990,991 A | 11/1976 | Gerstein | 252/542 |
| 4,003,699 A | 1/1977 | Rose et al. | 8/10.2 |
| 4,008,999 A | 2/1977 | Kalopissis | 8/410 |
| 4,217,914 A | 8/1980 | Jacquet et al. | 132/7 |
| 4,240,450 A | 12/1980 | Grollier et al. | 424/70 |
| 4,283,384 A | 8/1981 | Jacquet et al. | 424/47 |
| 4,330,291 A | 5/1982 | Bugaut et al. | 8/410 |
| 4,398,045 A | 8/1983 | Sebag | 568/624 |
| 4,445,521 A | 5/1984 | Grollier et al. | 132/7 |
| 4,526,781 A | 7/1985 | Goldberg et al. | 424/70 |
| 4,530,830 A | 7/1985 | McKaba et al. | 424/71 |
| 4,566,875 A | 1/1986 | Grollier et al. | 8/408 |
| 4,567,038 A | 1/1986 | Ciaudelli et al. | 424/59 |
| 4,567,039 A | 1/1986 | Stadnick et al. | 132/70 |
| 4,637,821 A | 1/1987 | Monnais et al. | 8/415 |
| 4,673,571 A | 6/1987 | Mahieu et al. | 8/406 |
| 4,685,931 A | 8/1987 | Schieferstein et al. | 8/406 |
| 4,714,610 A | 12/1987 | Gerstein | 424/70 |
| 4,776,855 A | 10/1988 | Pohl et al. | 8/406 |
| 4,828,819 A | 5/1989 | Lan et al. | 424/47 |
| 4,839,166 A | 6/1989 | Grollier et al. | 424/71 |
| 4,865,838 A | 9/1989 | Gross et al. | 8/406 |
| 4,892,916 A | 1/1990 | Hawe et al. | 526/304 |
| 4,904,275 A | 2/1990 | Grollier | 8/408 |
| 4,927,627 A | 5/1990 | Schrader et al. | 8/406 |
| 4,973,475 A | 11/1990 | Schnetzinger et al. | 424/70 |
| 4,986,983 A | 1/1991 | Gerstein | |
| 5,061,289 A | 10/1991 | Clausen et al. | 8/405 |
| 5,071,441 A | 12/1991 | Schnetzinger et al. | 8/405 |
| 5,100,658 A | 3/1992 | Bolich, Jr. et al. | 424/70 |
| 5,106,609 A | 4/1992 | Bolich, Jr. et al. | 424/70 |
| 5,122,273 A | 6/1992 | Rekers et al. | 210/500 |
| 5,163,010 A | 11/1992 | Klein et al. | 364/479 |
| 5,167,281 A | 12/1992 | Kalfoglou | 166/275 |
| 5,290,555 A | 3/1994 | Guthauser et al. | 424/401 |
| 5,304,370 A | 4/1994 | Hawkins et al. | 424/71 |
| 5,306,489 A | 4/1994 | Goldberg et al. | 424/71 |
| 5,374,420 A | 12/1994 | Gerstein | 424/70.11 |

(List continued on next page.)

FOREIGN PATENT DOCUMENTS

| | | |
|---|---|---|
| EP | 0074243 A1 | 3/1983 |
| EP | 133905 | 3/1985 |
| EP | 167866 | 1/1986 |
| EP | 168719 | 1/1986 |
| EP | 0074243 B1 | 11/1986 |
| EP | 0 216 479 | 4/1987 |
| EP | 0241707 | 10/1987 |
| EP | 533408 | 3/1993 |
| EP | 0650718 A1 | 5/1995 |
| EP | 0664114 A1 | 7/1995 |
| EP | 0673641 A1 | 9/1995 |
| EP | 0673641 B1 | 10/1996 |

(List continued on next page.)

OTHER PUBLICATIONS

Revlon Consumer Products Corporation "Further Observations" in European Opposition to EP 0827739. No date.

27 C.F.R. § 701.3 "Designation of Ingredients." No date.

(List continued on next page.)

Primary Examiner—Yogendra N. Gupta
Assistant Examiner—Eisa Elhilo
(74) Attorney, Agent, or Firm—Finnegan, Henderson, Farabow, Garrett & Dunner LLP

(57) ABSTRACT

The invention relates to an oxidation dye composition for keratin fibers, in particular for human keratin fibers such as the hair, this composition comprising, in a medium which is suitable for dyeing, at least one oxidation dye precursor and optionally one or more couplers, and also an anionic amphiphilic polymer containing at least one hydrophilic unit, and at least one allyl ether unit containing a fatty chain.

The invention also relates to dyeing processes and dyeing devices using the oxidation composition.

35 Claims, No Drawings

U.S. PATENT DOCUMENTS

| | | | |
|---|---|---|---|
| 5,376,146 A | 12/1994 | Casperson et al. | 8/405 |
| 5,380,340 A | 1/1995 | Neunhoeffer et al. | 8/409 |
| 5,389,363 A | 2/1995 | Snyder et al. | 427/70.7 |
| 5,391,368 A | 2/1995 | Gerstein | 424/70 |
| 5,393,305 A | 2/1995 | Cohen et al. | 8/406 |
| 5,409,630 A | 4/1995 | Lysy et al. | 252/174.23 |
| 5,443,855 A | 8/1995 | Wolf et al. | 424/401 |
| 5,489,431 A | 2/1996 | Ascione et al. | 424/401 |
| 5,519,063 A | 5/1996 | Mondet et al. | 514/772.4 |
| 5,534,267 A | 7/1996 | Neunhoeffer et al. | 424/701 |
| 5,605,678 A | 2/1997 | Ascione et al. | 424/59 |
| 5,607,664 A | 3/1997 | Ascione et al. | 424/59 |
| 5,663,366 A | 9/1997 | Neunhoeffer et al. | 548/371.4 |
| 5,735,908 A | 4/1998 | Cotteret et al. | 8/410 |
| 5,814,322 A | 9/1998 | Sebillotte-Arnaud | 424/401 |
| 5,843,193 A | 12/1998 | Hawkins et al. | 8/408 |
| 5,976,195 A | * 11/1999 | de la Mettrie et al. | 8/411 |
| 6,074,439 A | * 1/2000 | de la Mettrie et al. | 8/411 |

FOREIGN PATENT DOCUMENTS

| | | |
|---|---|---|
| EP | 0739620 A1 | 10/1996 |
| EP | 769 290 | 4/1997 |
| EP | 0650718 B1 | 3/1999 |
| EP | 0739620 B1 | 11/2000 |
| FR | 2 327 761 | 10/1976 |
| FR | 2446633 | 8/1980 |
| FR | 2 679 444 | 1/1993 |
| FR | 0 673 641 | 9/1995 |
| GB | 1026978 | 3/1963 |
| GB | 1153196 | 6/1966 |
| GB | 1066207 | 4/1967 |
| GB | 1236560 | 6/1971 |
| GB | 1257907 | 12/1971 |
| GB | 1541670 | 3/1979 |
| GB | 2124081 | 2/1984 |
| GB | 2192645 | 1/1988 |
| GB | 9526633 | 12/1996 |
| JP | 2-149509 | 12/1988 |
| JP | 01-165513 | 6/1989 |
| JP | 08268848 | 10/1996 |
| WO | 91/11985 | 8/1991 |
| WO | WO 91/15186 | 10/1991 |
| WO | WO 91/15187 | 10/1991 |
| WO | 93/21898 | 11/1993 |
| WO | 94/04125 | 3/1994 |
| WO | 97/24105 | 7/1997 |
| WO | 97/24106 | 7/1997 |
| WO | 97/24107 | 7/1997 |

OTHER PUBLICATIONS

Affidavit of Alan Paster No date.
Second Affidavit of Glenn Geardino No date.
Affidavit of Saroja Narasimhan No date.
Invoices from Rudy Patterson's Affidavit No date.
Exhibit A: Longer Lasting Formula Revlon Colorsilk® product: color photocopy of box listing ingredients No date.
Exhibit B: Longer Lasting Formula Revoln Colorsilk® product: color photocopy of product instruction sheet No date.
Exhibit C: Revlon Colorstay product: color photocopy of box listing ingredients No date.
Exhibit D: Revlon Colorstay product:color photocopy of product instruction sheet No date.
Cosmetic Research USA News Jan.–Feb. 1997 (1 page).
Cosmetic Research USA News Jan.–Feb. 1998 (1 page).
Exhibit E: New Improved Formula Revlon Colorsilk® product: color photocopy of box listing ingredients No date.
Exhibit F: New Improved Formula Revlon Colorsilk® product: color photocopy of product instruction sheet (®1997).
English Language Abstract of EP 0 673 641 9/95.
English Language Abstract of JP 88–169571 No date.
English Language Abstract of JP 91–333495 No date.
SN 08/923,969, filed Sep. 5, 1997.
SN 08/875,469, international application filed on Jul. 10, 1997: national stage entry: Jul. 29, 1997.
Wheeler et al., Instrumental colour assessment—Some Practical Experiences, J. Soc. Cosmet Chem 27:15–45(1976).
Comparative Tests OA 96183 SN 08/859,257, Natural Hair, 10 minutes (one page); Natural Hair, 30 min.(one page), Permed Hair, 10 minutes (one page) and Permed Hair, 30 minutes (one page).
Cosmetic Research USA News, Aug.–Sep. 1997, p. 118.
Holden, "Formulating Hair and Skin Products More Effectively," *Speciality Chemicals*, pp. 1–3. No date.
Results from Dialog search performed by Assignee, 83 pages. No date.
Results from Dialog search performed by Assignee, 19 pages. No date.
English language translation of JP 2–149,509, pp. 1–14. No date.
Webster's II New Riverside Dictionary, The Riverside Publishing Company, p. 365. No date.
Charles E. Jones Ph. D., "A Systematic Study of the Effect of Nonionic Hydrophobically–modified Ethoxylated Urethane Rheology Modifiers on Cationic Surfactants", Polymers in Cosmetics, ATTI DEL 20° Congresso Nazionale, Milan, Nov. 25, 1993, pp. 29–44.
"Rheology Modifiers for Personal Care Applications", Aculyn Personal Care Polymers, Rohm and Haas Company, Technical Bulletin FC–274a, Mar., 1994.
"Thickener Applications", Aculyn Personal Care Polymers, Rohm and Haas Company, Technical Bulletin, Mar., 1994.
"Aculyn® 44 Cosmetic Grade Rheology Modifier and Stabilizer", Aculyn Personal Care Polymers, Rohm and Haas Company, Technical Bulletin FC–309, Jul., 1994.
"Aculyn® Thickeners and Stabilizers", Aculyn Personal Care Polymers, Rohm and Haas Company, Technical Bulletin, Jul., 1994.
K. J. Saunders, "Organic Polymer Chemistry", Second Edition, Chapman and Hall, London, 1988, pp. 1–4.
Hans Batzer and Friedrich Lohse, Einführung in die makromolekulare Chemie, Hühig & Wepf Verlag, Basel, 1976, pp. 1–16.
Raymond B. Seymour and Charles E. Carraher, Jr., "Polymer Chemistry", An Introduction, Marcel Dekker, New York, 1981, pp. 1–12.
Proprietor's letter of Nov. 15, 2000 issued during examination of European patent application 97932885.3.
Y. Duccini, "New Polyurethane Rheology Modifiers for Cosmetics", undated. no date.
Y. Duccini, "New Rheology Modifiers for Chemical Household Products and Cosmetics", Pollena, 10, 353–361 (1993).

* cited by examiner

OXIDATION DYE COMPOSITION FOR KERATIN FIBERS, COMPRISING AN ANIONIC AMPHIPHILIC POLYMER

This is a continuation of application Ser. No. 09/436,985, filed Nov. 9, 1999 abandoned, which is a continuation of application Ser. No. 09/362,092, filed Jul. 28, 1999 abandoned, which is a continuation of application Ser. No. 09/292,965, filed Apr. 16, 1999 U.S. Pat. No. 6,074,439, which is a continuation of application Ser. No. 08/859,257, filed May 20, 1997 U.S. Pat. No. 5,976,195, all of which are incorporated herein by reference.

The present invention relates to an oxidation dye composition for keratin fibers, and in particular human keratin fibers such as the hair. The inventive composition comprises at least one oxidation dye precursor, optionally one or more couplers, and at least one anionic amphiphilic polymer containing at least one hydrophilic unit and at least one allyl ether unit containing a fatty chain.

It is known to dye keratin fibers, and in particular human hair, with dye compositions containing oxidation dye precursors, generally known as "oxidation bases", in particular ortho- or para-phenylenediamines, ortho- or para-aminophenols and heterocyclic bases.

Oxidation dye precursors are compounds that are initially colorless or only slightly colored, which develop their dyeing power on the hair in the presence of oxidizing agents, leading to the formation of colored compounds. The formation of these colored compounds results either from an oxidative condensation of the "oxidation bases" with themselves or from an oxidative condensation of the "oxidation bases" with color modifier compounds, or "couplers", which are generally present in the dye compositions used in oxidation dyeing and are represented more particularly by meta-phenylenediamines, meta-aminophenols, meta-diphenols, and certain heterocyclic compounds.

The variety of molecules used, which include, on the one hand, "oxidation bases" and, on the other hand, "couplers", allows a very broad range of colors to be obtained.

In order to localize the oxidation dye product to application on the hair so that it does not run down the face or outside of the areas which one wishes to dye, use has been made prior to this point in time of traditional thickeners such as crosslinked polyacrylic acid, hydroxyethylcelluloses, waxes or alternatively mixtures of nonionic surfactants with an HLB (hydrophilic-lipophilic balance) which, when suitably chosen, bring about a gelling effect when they are diluted with water and/or surfactants.

However, the inventors have observed that the ingredients of the traditional thickener, surfactant and solvent type generally decrease the uptake of the dye on the fibers, which is reflected by a dull shade and also by the necessary use of more dye, solvent and/or surfactants to solubilize the dye if it is desired to obtain an intense shade. Moreover, the inventors have also observed that after mixing with an oxidant, the dye compositions containing the oxidation dye precursor or precursors and optionally the coupler or couplers, and also the above-mentioned ingredients, lost some of their gelled nature and consequently led to undesirable running.

Now, after considerable research conducted in this direction, the inventors have discovered that it is possible to obtain oxidation dye compositions (after mixing with the oxidant) which do not run and therefore remain better localized at the point of application, and which also make it possible to obtain more chromatic (more luminous) shades while at the same time being appreciably intense, if an effective amount of an anionic amphiphilic polymer containing at least one hydrophilic unit and at least one allyl ether unit containing a fatty chain, are introduced (i) either into the composition containing the oxidation dye precursor or precursors and optionally the coupler or couplers [or composition. (A)], or (ii) into the oxidizing composition [or composition (B)], or (iii) into both compositions at the same time.

For purposes of the present invention, the chromaticity (luminosity) is defined by the value $c^*$ in the $L^*$, $a^*$, $b^*$ calorimetric notation system of the Commission Internationale de l'Eclairage (C.I.E.) [International Lighting Commission]. This value ($c^*$) is equal to the square root of the sum $a^2+b^2$ (+a is red, −a is green, +b is yellow, −b is blue). The shade is proportionately more luminous the higher the value of $c^*$.

In this system of notation, $L^*$ defines the intensity of the shade. The shade is proportionately more intense the smaller the value of $L^*$ (0=black, 100=white).

These discoveries form the basis of the present invention.

A subject of the present invention is thus an oxidation dye composition for keratin fibers, in particular for human keratin fibers such as the hair, this composition comprising, in a medium which is suitable for dyeing, at least one oxidation dye precursor (oxidation base) and, where appropriate, one or more couplers, which composition is characterized in that it also contains at least one anionic amphiphilic polymer containing at least one hydrophilic unit and at least one allyl ether unit containing a fatty chain.

By means of the present invention, it is also possible, advantageously, to reduce the consumption of surfactants, or even to dispense with them altogether.

The present invention also makes it possible to decrease the amount of active coloring materials used in the dye compositions, relative to conventional techniques known in the prior art.

Another subject of the present invention relates to a ready-to-use composition for dyeing keratin fibers, which contains at least one oxidation dye precursor and optionally at least one coupler, and at least one anionic amphiphilic polymer containing at least one hydrophilic unit and at least one allyl ether unit containing a fatty chain, and an oxidizing agent.

The invention is also directed towards a process for dyeing keratin fibers, and in particular human keratin fibers such as the hair, this process comprising applying to these fibers at least one composition (A1) containing, in a medium which is suitable for dyeing, at least one oxidation dye precursor and optionally at least one coupler, in combination with at least one anionic amphiphilic polymer containing at least one hydrophilic unit and at least one allyl ether unit containing a fatty chain, the color being developed at alkaline, neutral or acidic pH using an oxidizing agent which is mixed with the composition (A1) only at the time of use or which is present in a composition (B1) that is applied sequentially without intermediate rinsing.

The invention is also directed towards a variant of the above process, which comprises applying to the fibers at least one composition (A2) containing, in a medium which is suitable for dyeing, at least one oxidation dye precursor and optionally at least one coupler, and doing so in the presence or absence of an anionic amphiphilic polymer containing at least one hydrophilic unit and at least one allyl ether unit containing a fatty chain, the color being developed at alkaline, neutral or acidic pH using an oxidizing composition (B2) which contains an oxidizing agent and an effective amount of at least one anionic amphiphilic polymer containing at least one hydrophilic unit and at least one allyl ether unit containing a fatty chain. Composition (B2) is mixed with composition (A2) only at the time of use or is applied sequentially without intermediate rinsing.

Another subject of the invention is multi-compartment dyeing devices or "kits", a first compartment of which contains at least one oxidation dye precursor, optionally at least one coupler, and at least one anionic amphiphilic polymer containing at least one hydrophilic unit and at least one allyl ether unit containing a fatty chain, and a second compartment of which contains an oxidizing agent.

According to another variant, the present invention also includes multi-compartment dyeing devices or "kits", a first compartment of which contains at least one oxidation dye precursor, optionally at least one coupler, and does so in the presence or absence of anionic amphiphilic polymer containing at least one hydrophilic unit and at least one allyl ether unit containing a fatty chain, and a second compartment of which contains an oxidizing agent and an effective amount of at least one anionic amphiphilic polymer containing at least one hydrophilic unit and at least one allyl ether unit containing a fatty chain.

The invention also relates to the use of the oxidation dye composition defined above or a multi-compartment dyeing device or "kit" as defined above in, order to dye human keratin fibers such as the hair.

Other characteristics, aspects, objects and advantages of the invention will become even more apparent on reading the description and the examples which follow.

The anionic amphiphilic polymers containing at least one hydrophilic unit and at least one allyl ether unit containing a fatty chain which are used according to the invention are preferably selected from those in which the hydrophilic unit contains an ethylenic unsaturated anionic monomer, more particularly a vinyl carboxylic acid and most particularly an acrylic acid, a methacrylic acid or mixtures thereof, and whose allyl ether unit containing a fatty chain corresponds to the monomer of formula (I) below:

$$CH_2=CR'CH_2OB_nR \qquad (I)$$

in which R' denotes H or $CH_3$, B denotes the ethylenoxy radical, n is zero or denotes an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms.

A unit of formula (I) more particularly preferred according to the present invention is a unit in which R' denotes H, n is equal to 10 and R denotes a stearyl (C18) radical.

Anionic amphiphilic polymers of this type are described and prepared, according to an emulsion polymerization process in European Patent EP-0,216,479 B2, the disclosure of which is hereby incorporated by reference.

Among these anionic amphiphilic polymers, polymers formed of 20 to 60% by weight acrylic acid and/or methacrylic acid, of 5 to 60% by weight lower alkyl (meth)acrylates, of 2 to 50% by weight allyl ether containing a fatty chain of formula (I), and of 0 to 1% by weight of a crosslinking agent which is a well-known copolymerizable polyethylenic unsaturated monomer, for instance diallyl phthalate, allyl (meth)acrylate, divinylbenzene, (poly)ethylene glycol dimethacrylate and methylenebisacrylamide, are more particularly preferred according to the invention.

Among the latter, crosslinked terpolymers of methacrylic acid, of ethyl acrylate, of polyethylene glycol (10 EO) ether of stearyl alcohol (Steareth 10), in particular those sold by the company Allied Colloids under the names SALCARE SC 80 and SALCARE SC90, which are aqueous emulsions containing 30% of a crosslinked terpolymer of methacrylic acid, of ethyl acrylate and of steareth-10 allyl ether (40/50/10), are most particularly preferred.

The anionic amphiphilic polymers containing at least one hydrophilic unit and at least one allyl ether unit containing a fatty chain according to the invention are preferably used in an amount which may range approximately from 0.05 to 10% by weight relative to the total weight of the dye composition applied to the fibers. More preferably, this amount varies approximately from 0.2 to 5% by weight.

The oxidation dye precursors which can be used in the context of the present invention are selected from those known conventionally in oxidation dyeing and among which mention may be made in particular of:

para-phenylenediamines of formula (II) below, and acid-addition salts thereof:

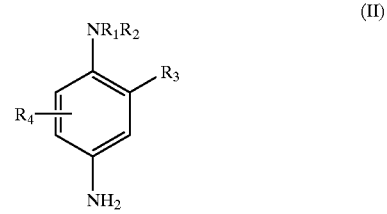

(II)

in which:
R$_1$ represents a hydrogen atom, a $C_1$–$C_4$ alkyl radical, a $C_1$–$C_4$ monohydroxyalkyl radical, a $C_2$–$C_4$ polyhydroxyalkyl radical or a 4'-aminophenyl radical, R$_2$ represents a hydrogen atom or a $C_1$–$C_4$ alkyl radical, a $C_1$–$C_4$ monohydroxyalkyl radical or a $C_2$–$C_4$ polyhydroxyalkyl radical, R$_3$ represents a hydrogen atom, a halogen atom such as a chlorine atom, or a $C_1$–$C_4$ alkyl radical, a sulpho radical, a carboxyl radical, a $C_1$–$C_4$ monohydroxyalkyl radical or a $C_1$–$C_4$ hydroxyalkoxy radical, and R$_4$ represents a hydrogen atom or a $C_1$–$C_4$ alkyl radical.

Among the para-phenylenediamines of formula (II) above, mention may be made more particularly of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-paraphenylenediamine, N,N-dimethyl-para-phenylenediamine, N,N-diethyl-paraphenylenediamine, N,N-dipropyl-para-phenylenediamine, 4-amino-N,N-diethyl-3-methylaniline, N,N-bis(βhydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and acid-addition salts thereof.

Among the para-phenylenediamines of formula (II) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine. 2,6-diethyl-para-phenylenediamine, 2,3-dimethyl-para-phenylenediamine, N,N-bis(β-hydroxyethyl)-para-phenylenediamine and 2-chloro-para-phenylenediamine, and acid-addition salts thereof, are most particularly preferred.

bis(phenyl)alkylenediamines corresponding to formula (III) below, and acid-addition salts thereof:

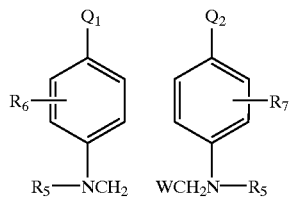

(III)

in which:
Q$_1$ and Q$_2$, which may be identical or different, represent a hydroxyl radical or NHR$_8$ in which R$_8$ represents a hydrogen atom or a C$_1$–C$_4$ alkyl radical,
R$_5$ represents a hydrogen atom, a C$_1$–C$_4$ alkyl radical, a C$_1$–C$_4$ monohydroxyalkyl radical, a C$_2$–C$_4$ polyhydroxyalkyl radical or a C$_1$–C$_4$ aminoalkyl radical in which the amino residue may be substituted,
R$_6$ and R$_7$, which may be identical or different, represent a hydrogen or halogen atom or a C$_1$–C$_4$ alkyl radical,
W represents a radical taken from the group consisting of the following radicals: —(CH$_2$)$_n$—; —(CH$_2$)$_m$—O—(CH$_2$)$_m$—; (CH$_2$)$_m$—CHOH—(CH$_2$)$_m$—; and

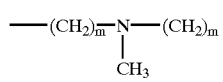

in which n is an integer from 0 to 8 and m is an integer from 0 and 4.

Among the bis(phenyl)alkylenediamines of formula (III) above, mention may be made more particularly of N,N'-bis(β-hydroxyethyl)-N,N'-bis(4'-aminophenyl)-1,3-diamino-2-propanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis(4-aminophenyl)tetra-methylenediamine, N,N'-bis(4-methylaminophenyl)tetra-methylenediamine, N,N'-bis(ethyl)-N,N'-bis(4'-amino-3'-methylphenyl)ethylenediamine, as well as acid-addition salts thereof.

Among these bis(phenyl)alkylenediamines of formula (III), N,N'-bis(β-hydroxyethyl)-N,N'-bis(4'-aminophenyl)-1,3-diamino-2-propanol or one of the acid-addition salts thereof is particularly preferred.

para-aminophenols corresponding to formula (IV) below, and acid-addition salts thereof:

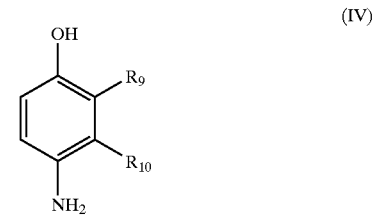

(IV)

in which:
R$_9$ represents a hydrogen atom, a C$_1$–C$_4$ alkyl radical, a C$_1$–C$_4$ monohydroxyalkyl radical, a (C$_1$–C$_4$)alkoxy-(C$_1$–C$_4$)alkyl radical, a C$_1$–C$_4$ aminoalkyl radical or a (C$_1$–C$_4$)hydroxyalkyl(C$_1$–C$_4$)aminoalkyl radical;
R$_{10}$ represents a hydrogen or fluorine atom, a C$_1$–C$_4$ alkyl radical, a C$_1$–C$_4$ monohydroxyalkyl radical, a C$_2$–C$_4$ polyhydroxyalkyl radical, a C$_1$–C$_4$ aminoalkyl radical, a C$_1$–C$_4$ cyanoalkyl radical or a (C$_1$–C$_4$)alkoxy(C$_1$–C$_4$)alkyl radical, it being understood that at least one of the radicals R$_9$ or R$_{10}$ represents a hydrogen atom.

Among the para-aminophenols of formula (IV)-above, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and acid-addition salts thereof, may be mentioned more particularly.

the ortho-aminophenols which can be used as oxidation bases in the context of the present invention are selected in particular from 2-aminophenol, 2-amino-1-hydroxy-5-methylbenzene, 2-amino-1-hydroxy-6-methylbenzene and 5-acetamido-2-aminophenol, and acid-addition salts thereof.

the heterocyclic bases which can be used as oxidation bases in the context of the present invention are selected in particular from pyridine derivatives, pyrimidine derivatives and pyrazole derivatives, and acid-addition salts thereof.

Among the pyridine derivatives, mention may be made more particularly of the compounds described, for example, in patents GB-1,026,978 and GB-1,153,196, the disclosures of which are hereby incorporated by reference, such compounds being, for instance, 2,5-diaminopyridine and acid-addition salts thereof.

Among the pyrimidine derivatives, mention may be made more particularly of the compounds described, for example, in German patent DE-2,359,399 or Japanese patents JP-88-169,571 and JP-91-333,495, the disclosures of which are hereby incorporated by reference, such compounds being, for instance, 2,4,5,6-tetraaminopyrimidine and 4-hydroxy-2,5,6-triaminopyrimidine and acid-addition salts thereof.

Among the pyrazole derivatives, mention may be made more particularly of the compounds described in German patents DE-3,843,892 and DE-4,133,957 and PCT patent applications WO-94/08969 and WO-94/08970, the disclosures of which are hereby incorporated by reference, such compounds being, for instance, 4,5-diamino-1-methylpyrazole, 3,4-diaminopyrazole and 4,5-diamino-1-(4'-chlorobenzyl)pyrazole, and acid-addition salts thereof.

According to the invention, the oxidation base or bases preferably represent from 0.0005 to 12% by weight approximately relative to the total weight of the composition (A) and even more preferably from 0.005 to 6% by weight approximately.

The couplers which can be used in the dyeing process according to the invention are those used conventionally in oxidation dye compositions, i.e., meta-phenylenediamines, meta-aminophenols and meta-diphenols, mono- or polyhydroxylated naphthalene derivatives, sesamol and derivatives thereof and heterocyclic compounds such as, for example, indole couplers, indoline couplers, pyridine couplers and acid-addition salts thereof.

These couplers may be selected in particular from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one and 1-phenyl-3-methylpyrazol-5-one, and acid-addition salts thereof.

When they are present, these couplers preferably represent from 0.0001 to 10% by weight approximately relative to the total weight of the composition (A), and even more preferably from 0.005 to 5% by weight approximately.

In general, the acid-addition salts of the oxidation bases and couplers are selected in particular from the hydrochlorides, hydrobromides, sulphates, tartrates, lactates and acetates.

The composition (A) may also contain, in addition to the oxidation dye precursors defined above and the couplers combined optionally therewith, direct dyes to enrich the shades with glints. These direct dyes may then be selected in particular from nitro, azo and anthraquinone dyes.

The composition (A) and/or the composition (B) also more particularly contains at least one cationic or amphoteric substantive polymer as defined on pages 3 and 4 of European patent application EP-0,673,641 A1, the disclosure of which is hereby incorporated by reference, and for which it is advantageously preferred to use:

the quaternary polyammonium polymers prepared and described in French patent 2,270,846, the disclosure of which is hereby incorporated by reference, containing repeating units corresponding to formula (V) below:

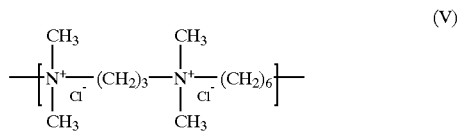

and whose molecular weight, determined by gel permeation chromatography, ranges from 9500 to 9900;

the quaternary polyammonium polymers prepared and described in French patent 2,270,846, the disclosure of which is hereby incorporated by reference, containing repeating units corresponding to formula (VI) below:

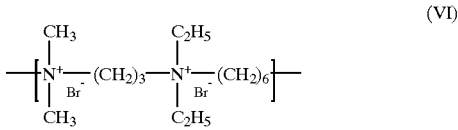

and whose molecular weight, determined by gel permeation chromatography, is about 1200.

The medium for composition (A) which is suitable for dyeing is preferably an aqueous medium containing water and which optionally contains cosmetically acceptable organic solvents including, more particularly, alcohols such as ethyl alcohol, isopropyl alcohol, benzyl alcohol and phenylethyl alcohol, glycols or glycol ethers such as, for example, the monomethyl, monoethyl and monobutyl ethers of ethylene glycol, propylene glycol or ethers thereof such as, for example, propylene glycol monomethyl ether, butylene glycol, dipropylene glycol and diethylene glycol alkyl ethers such as, for example, diethylene glycol monoethyl ether or monobutyl ether, in concentrations of approximately from 0.5 to 20% and preferably approximately from 2 to 10% by weight relative to the total weight of the composition.

The composition (A) may also contain an effective amount of other agents, previously known elsewhere in oxidation dyeing, such as various common adjuvants, for instance sequestering agents, hair conditioners and in particular silicones, preserving agents, opacifiers, etc., and optionally anionic, nonionic or amphoteric surfactants or mixtures thereof.

The composition (A) may also contain antioxidants. These may be selected in particular from sodium sulphite, thioglycolic acid, thiolactic acid, sodium bisulphite, dehydroascorbic acid, hydroquinone, 2-methylhydroquinone, tert-butylhydroquinone and homogentisic acid, and they are then generally present in amounts ranging approximately from 0.05 to 1.5% by weight relative to the total weight of the composition.

Obviously, a person skilled in the art will take care to select the optional additional compound or compounds mentioned above, such that the advantageous properties intrinsically associated with the dye composition according to the invention are not, or are substantially not, adversely affected by the addition or additions envisaged.

In the composition (B), the oxidizing agent is preferably selected from urea peroxide, alkali metal bromates or ferricyanides, and persalts such as perborates, percarbonates and persulphates. The use of hydrogen peroxide is particularly preferred.

The composition (B) advantageously contains an aqueous hydrogen peroxide solution whose titre may range, more particularly, approximately from 2.5 to 40 volumes, and even more preferably approximately from 5 to 20 volumes.

The pH of the ready-to-use composition applied to the keratin fibers [composition resulting from mixing the dye composition (A) and the oxidizing composition (B)] generally ranges from 4 to 11. The pH preferably ranges from 6 to 10, and may be adjusted to the desired value using acidifying or basifying agents that are well known in the state of the art in the dyeing of keratin fibers.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and compounds of formula (VII) below:

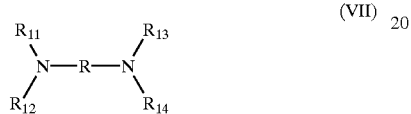

(VII)

in which R is a propylene residue optionally substituted with a hydroxyl group or a $C_1$–$C_4$ alkyl radical; $R_{11}$, $R_{12}$, $R_{13}$ and $R_{14}$, which may be identical or different, represent a hydrogen atom, a $C_1$–$C_4$ alkyl radical or a $C_1$–$C_4$ hydroxyalkyl radical.

The acidifying agents are conventionally, by way of example, inorganic or organic acids such as hydrochloric acid, orthophosphoric acid, carboxylic acids is such as tartaric acid, citric acid or lactic acid, and sulphonic acids.

The dyeing process according to the invention preferably comprises applying a mixture, prepared at the time of use from the compositions (A) and (B) described above, onto the wet or dry keratin fibers and in leaving it to act for an exposure time preferably ranging from 1 to 60 minutes approximately, and more preferably from 10 to 45 minutes approximately, rinsing the fibers, optionally washing them with shampoo and rinsing them again and drying them.

Concrete examples illustrating the invention will now be given without, however, being limiting in nature.

EXAMPLE 1

The following dye composition, in accordance with the invention, was prepared:

Methacrylic acid/ethyl acrylate/steareth-10 allyl ether crosslinked anionic polymer, sold as an aqueous emulsion containing 30% AM* (SALCARE SC 80 from Allied Colloids) . . . 1.0 g AM*
Oleic acid . . . 3.0 g
Aqueous solution of sodium bisulphite containing 35% AM* . . . 0.45 g AM*
Para-phenylenediamine . . . 0.162 g
Resorcinol . . . 0.165 g
Aqueous ammonia (20% $NH_3$) . . . 11.5 g
Sequestering agent . . . q.s.
Water . . . q.s. 100 g
AM*=active material This composition was mixed weight for weight, at the time of use, with 20-volumes aqueous hydrogen peroxide solution and the mixture obtained was then applied to locks of natural hair containing 90% white hairs.

After an exposure time of 10 minutes, the locks were rinsed and were then washed with a shampoo, rinsed again and then dried.

Using an I.C.S. spectrocolorimeter, the chromaticity c* of the shade was measured from the values of a* and b* in the C.I.E. L*, a*, b* international color notation system.

The result was as follows: c*=14.27.

The value L* of the shade was also measured.

The result was as follows: L*=46.77.

COMPARATIVE EXAMPLE 2

Example 1 was repeated, replacing 1 gram of methacrylic acid/ethyl acrylate/steareth-10 allyl ether crosslinked anionic amphiphilic polymer (SALCARE SC 80) by the mixture of the following two nonionic surfactants (which allows the same viscosity to be obtained):

18 grams of decyl alcohol ($C_{10}$-$C_{21}$-$C_{14}$/85-8.5-6.5) oxyethylenated with 3.5 mol of ethylene oxide, sold under the name MERGITAL BL 309 by the company Henkel, and 12 grams of decyl alcohol ($C_{10}$-$C_{21}$-$C_{14}$/85-8.5-6.5) oxyethylenated with 5.5 mol of ethylene oxide, sold under the name MERGITAL BL 589 by the company Henkel.

The same procedure as in Example 1 was then followed.

The results were as follows: c*=12.86

L*=49.72

CONCLUSION FROM THESE EXAMPLES

The shade obtained using a dye composition according to the invention was more luminous (larger value of c*) than that obtained using a dye composition according to the prior art; it is also more intense (smaller value of L*).

We claim:

1. A composition for the oxidative dyeing of keratin fibres comprising
    (a) a first component comprising:
        at least one oxidative dye precursor comprising at least one ortho-phenylenediamine, para-phenylenediamine, bis(phenyl)alkylenediamine, ortho-aminophenol, para-aminophenol, heterocyclic base, or acid-addition salt of any of the foregoing; and
        at least one anionic amphiphilic polymer comprising at least one hydrophilic unit and at least one allyl ether unit comprising a fatty chain; and
    (b) a second component comprising an oxidizing composition.

2. A composition according to claim 1, wherein said at least one anionic amphiphilic polymer comprising at least one hydrophilic unit and at least one allyl ether unit comprising a fatty chain, is present in an amount ranging from 0.05 to 10% by weight relative to the total weight of the composition.

3. A composition according to claim 2, wherein said at least one polymer comprising at least one hydrophilic unit and at least one allyl ether unit comprising a fatty chain, is present in an amount ranging from 0.2 to 5% by weight relative to the total weight of the composition.

4. A composition according to claim 1, wherein said at least one hydrophilic unit comprises at least one ethylenic unsaturated anionic unit.

5. A composition according to claim 4, wherein said at least one hydrophilic unit comprises at least one vinyl carboxylic acid.

6. A composition according to claim 4, wherein said at least one hydrophilic unit comprises at least one acrylic acid.

7. A composition according to claim 4, wherein said at least one hydrophilic unit comprises at least one methacrylic acid.

8. A composition according to claim 1, wherein said allyl ether unit comprising a fatty chain is formed from a monomer of formula (I):

$$CH_2=CR'CH_2OB_nR \quad (I)$$

in which R' is H or $CH_3$, B is an ethylenoxy radical, n is zero or denotes an integer ranging from 1 to 100, and R is a hydrocarbon radical selected from alkyl and cycloalkyl radicals, having from 8 to 30 carbon atoms.

9. A composition according to claim 8, wherein said hydrocarbon radical is an alkyl radical having 10 to 24 carbon atoms.

10. A composition according to claim 8, wherein in formula (I), R' is H, n is equal to 10, and R is a stearyl radical.

11. A composition according to claim 1, wherein said anionic amphiphilic polymer is formed by emulsion polymerization of (a) from 20 to 60% by weight acrylic acid or methacrylic acid, (b) from 5 to 60% by weight lower alkyl (meth)acrylates, and (c) from 2 to 50% by weight allyl ether comprising a fatty chain of formula (I)

$$CH_2=CR'CH_2OB_nR \quad (I)$$

in which R' is H or $CH_3$, B is an ethylenoxy radical, n is zero or is an integer ranging from 1 to 100, and R is a hydrocarbon radical selected from alkyl and cycloalkyl radicals, having from 8 to 30 carbon atoms, and from 0 to 1% of a crosslinking agent.

12. A composition according to claim 11, wherein said anionic amphiphilic polymer is a crosslinked polymer comprising (a) 40% by weight methacrylic acid, (b) 50% by weight ethyl acrylate, and (c) 10% by weight polyethylene glycol ether of stearyl alcohol.

13. A composition according to claim 1, wherein the at least one ortho-phenylenediamine, para-phenylenediamine, bis(phenyl)alkylenediamine, ortho-aminophenol, para-aminophenol, heterocyclic base, or acid-addition salt of any of the foregoing is present in an amount ranging from 0.0005 to 12% by weight relative to the total weight.

14. A composition according to claim 1, wherein said first component further comprises at least one coupler.

15. A composition according to claim 14, wherein said at least one coupler is chosen from at least one meta-phenylenediamine, meta-aminophenol, meta-diphenol, heterocyclic coupler, or acid addition salt of any of the foregoing.

16. A composition according to claim 15, wherein said at least one coupler is present in an amount ranging from 0.0001 to 10% by weight relative to the total weight of the composition.

17. A composition according to claim 1, wherein said acid addition salt of said at least one ortho-or para-phenylenediamine, bis(phenyl)alkylenediamine, ortho-aminophenol, para-aminophenol, or heterocyclic base, is selected from hydrochloride, hydrobromide, sulphate, tartrate, lactate, and acetate.

18. A composition according to claim 1, further comprising at least one polymer selected from a cationic polymer and an amphoteric polymer.

19. A composition according to claim 18, wherein said polymer is a quaternary polyammonium polymer comprising repeating units of formula (V):

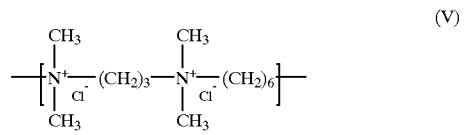

20. A composition according to claim 18, wherein said polymer is a quaternary polyammonium polymer comprising repeating units of formula (VI):

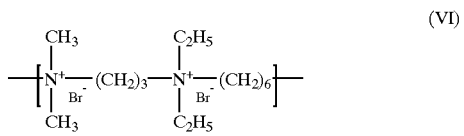

21. A composition according to claim 1, wherein said first component further comprises at least one reducing agent present in an amount ranging from 0.05 to 3 percent by weight relative to the total weight of the first component.

22. A process for oxidative dyeing of keratin fibres comprising:
  (a) combining at the time of use, a first component comprising:
    at least one oxidative dye precursor comprising at least one ortho-phenylenediamine, para-phenylenediamine, bis(phenyl)alkylenediamine, ortho-aminophenol, para-aminophenol, heterocyclic base, or acid-addition salt of any of the foregoing; and
    at least one anionic amphiphilic polymer comprising at least one hydrophilic unit and at least one allyl ether unit comprising a fatty chain; with
  (b) an effective amount of an oxidizing composition; and
applying the resulting mixture to the keratin fibres in a medium suitable for dyeing.

23. A process for oxidative dyeing of keratin fibres comprising:
  (a) applying to the keratin fibres in a medium suitable for dyeing a first component comprising:
    at least one oxidative dye precursor comprising at least one ortho-phenylenediamine, para-phenylenediamine, bis(phenyl)alkylenediamine, ortho-aminophenol, para-aminophenol, heterocyclic base, or acid-addition salt of any of the foregoing; and
    at least one anionic amphiphilic polymer comprising at least one hydrophilic unit and at least one allyl ether unit comprising a fatty chain: and
  (b) applying to the keratin fibers a second component comprising:
    an effective amount of an oxidizing composition
    wherein the first component is not rinsed from the keratin fibers prior to applying the second component.

24. A process according to claim 22, wherein said resulting mixture has a pH ranging from 4 to 11.

25. A process according to claim 22, wherein said oxidizing composition comprises an oxidizing agent selected from hydrogen peroxide, urea peroxide, alkali metal bromates, ferricyanides, and persalts.

26. A process according to claim 23, wherein said oxidizing composition comprises an oxidizing agent selected from hydrogen peroxide, urea peroxide, alkali metal bromates, ferricyanides, and persalts.

27. A process according to claim 25, wherein said oxidizing agent is hydrogen peroxide in solution having a titre ranging from 2.5 to 40 volumes.

28. A process according to claim 26, wherein said oxidizing agent is hydrogen peroxide in solution having a titre ranging from 2.5 to 40 volumes.

29. A process according to claim 25, wherein said oxidizing composition further comprises at least one anionic amphiphilic polymer comprising at least one hydrophilic unit and at least one allyl ether unit comprising a fatty chain.

30. A process according to claim 26, wherein said oxidizing composition further comprises at least one anionic amphiphilic polymer comprising at least one hydrophilic unit and at least one allyl ether unit comprising a fatty chain.

31. A process according to claim 25 wherein said medium suitable for dyeing is acid, neutral, or alkaline.

32. A process according to claim 26 wherein said medium suitable for dyeing is acid, neutral, or alkaline.

33. A multi-compartment device or kit for oxidative dyeing of keratin fibres, said kit comprising at least two compartments, one of said compartments containing a composition, in a medium which is suitable for dyeing, comprising:

at least one oxidative dye precursor comprising at least one ortho-phenylenediamine, para-phenylenediamine, bis(phenyl)alkylenediamine, ortho-aminophenol, para-aminophenol, heterocyclic base, or acid-addition salt of any of the foregoing; and at least one anionic amphiphilic polymer comprising at least one hydrophilic unit and at least one allyl ether unit comprising a fatty chain; and second of said compartments comprising:

an oxidizing agent.

34. A multi-compartment kit according to claim 33, wherein said oxidizing agent is additionally combined with at least one anionic amphiphilic polymer comprising at least one hydrophilic unit and at least one allyl ether unit comprising a fatty chain.

35. A multi-compartment kit according to claim 33, wherein said keratin fibres are human hair.

* * * * *